United States Patent [19]

Tusa et al.

[11] 3,939,099

[45] Feb. 17, 1976

[54] FRAGRANCE COMPOSITION

[75] Inventors: Philip Tusa, Madison; Frank Tranner, Trumbull, both of Conn.

[73] Assignee: Chesebrough-Pond's, Inc., Greenwich, Conn.

[22] Filed: Dec. 26, 1974

[21] Appl. No.: 536,396

[52] U.S. Cl. ............ 252/522; 252/DIG. 5; 252/316; 260/66; 424/273
[51] Int. Cl.² .................... A61K 2/46; C11B 9/00
[58] Field of Search .................................... 252/522

[56] References Cited
UNITED STATES PATENTS

| | | | |
|---|---|---|---|
| 3,417,054 | 12/1968 | Merijan et al. | 260;424/66;78 X |
| 3,455,838 | 7/1969 | Marotta et al. | 252/522 X |
| 3,567,118 | 3/1971 | Shepherd et al. | 252/522 X |
| 3,567,119 | 3/1971 | Wilbert et al. | 252/522 X |
| 3,596,833 | 8/1971 | Gould | 252/522 X |
| 3,697,644 | 10/1972 | Laiderman | 424/70 |
| 3,776,920 | 12/1973 | D'Amico | 424/273 X |

*Primary Examiner*—Herbert Levine
*Assistant Examiner*—G. E. Schmitkons
*Attorney, Agent, or Firm*—Morgan, Finnegan, Pine, Foley & Lee

[57] ABSTRACT

The fragrance composition of this invention comprises the combination of a fragrance oil and a film-former which are mutually soluble in a water-ethanol solvent. Fragrance compositions of the aforedescribed type have an adequate odor strength when initially applied to a substrate (e.g., human skin), which odor strength is continued for a desirably long period of time after application.

10 Claims, No Drawings

FRAGRANCE COMPOSITION

This invention relates to a novel fragrance composition (e.g., perfume, cologne, etc.) having a desirable odor strength when initially applied to the skin of a user and which odor strength is continued for a desirably long period of time after application.

The fragrance composition of this invention comprises the combination of a fragrance oil and a film-former which are mutually soluble in a water-ethanol solvent. The aforementioned components are in such relative amounts that the fragrance compositions exhibit the following characteristics:

1. The fragrance composition has an adequate odor strength when it is initially applied to the skin of the user, which odor strength remains at a satisfactory level for a long period of time.

2. Both the fragrance compound oil and the film-former are co-dissolved in the volatile solvent so as to provide a mutual compatible system.

3. During evaporation of the volatile solvent, a sufficient amount of fragrance oil is released to impart the desired odor level but at a rate where a desired odor level is maintained for a prolonged period of time.

BACKGROUND PRIOR ART

It is known that with conventional fragrance compositions, such as perfumes and colognes, the initial odor of the fragrance compound is very great and sometimes overpowering. However, within a reasonably short period of time, that is several hours, the odor strength of the applied fragrance compound begins to diminish and becomes progressively weaker. After a period of time, very little odor remains.

Prior to this invention, various techniques have been proposed for prolonging the odor of fragrance compositions. One such procedure is based on the knowledge that the rate at which a fragrance volatilizes may be reduced by the addition of a compatible oil having a vapor pressure lower than that of the fragrance oil. The volatility of the fragrance is thereupon reduced by the ratio of the mole fraction of the fragrance to the sum of the mole fractions of the fragrance oil and diluent oil. This method has several disadvantages. One disadvantage is that an inordinate amount of fragrance oil must be used in order to overcome the initial fragrance depression. Said increase in concentration will result in a higher cost of ingredients and, in some cases, an increase in skin irritation since some fragrance materials have shown potential irritation in the past. A second disadvantage would be that on application to the skin an oil film would be deposited on the skin which is objectionable.

The present state of the art also teaches that the volatility of the fragrance oil is reduced, and may even be overcome, by surrounding small droplets of fragrance oil by a resistant wall. This wall or encapsulation may be either water sensitive or water insensitive. In the first case, the fragrance is released when the encapsulated particle is affected by water but not insensible moisture loss from the skin; while in the second case, the capsule wall must be ruptured mechanically (as by scratching) before the fragrance is released. Encapsulating processes and compositions are well known. Examples of prior art publications and patents which teach the aforementioned encapsulating procedures for prolonging fragrance release are the following:

German Patent No. 1,268,316.

"Coacervation," micro-encapsulage et produits microencapsules,

G. J. Leeuw, Parf. Cosm. Sav., Vol. 13, No. 5, May 1970.

U.S. Pat. No. 3,539,465.

Ecapsulated Perfume in Aerosol Products, Polak's Frutal Works, Journal Society Cosmetic Chemists, Vol. 22, pp. 655–666, Sept. 17, 1971.

U.S. Pat. No. 3,455,838. Microencapsulation, L. A. Luzzi, Journal of Pharmaceutical Sciences, Vol. 59, No. 1, Oct. 1970.

Prior to this invention, it was known to use film-formers of the type used in accordance with this invention in cosmetic compositions (e.g., skin and hair treating compositions) to effect an improvement upon application to the body (e.g., to provide a smooth coating, minimize undesirable side effects, etc.). Examples of patents showing compositions of the aforementioned type are U.S. Pat. Nos. 3,697,644; 3,776,920 and 3,417,054. Film-formers of the type used in accordance with this invention have also been used in fiber or fabric treating compositions to impart to the fiber or fabric odorant or fragrant qualities. Compositions of the aforementioned type are shown in U.S. Pat. Nos. 3,567,118; 3,567,119 and 3,596,833.

None of the above-mentioned prior art patents or publications teach applicants' novel composition which provides a perfume or fragrance composition wherein the initial odor strength of the fragrance composition is at an acceptable, effective but not overpowering level, and which odor strength is not rapidly diminished but remains noticeable for a long period of time. One of the main objects of the invention is to provide a perfume or fragrance composition which is at an acceptable odor strength immediately upon application and which advantageously does not significantly lose its odor strength for a long period after application. This is in contrast to many conventional fragrance compositions whose initial odor character, while initially acceptable, rapidly diminishes after a short period of time when exposed on the skin. The fragrance compositions of this invention also are distinguished from prior art compositions which initially have no or little odor strength upon application to a substrate and which only becomes noticeable upon activation.

It has been found that the objectives of this invention may be realized if a fragrance compound oil is combined with a film-former in a water-alcohol solvent in such amounts that there results a completely soluble, mutually compatible system. Discreet encapsulation and granulation processes are avoided. A smooth film, invisible to the eye, free from powder-like residue, is laid down on the skin. A more stable system results since the fragrance/polymer complex is formed on the skin eliminating possibility of encapsulation breakdown and subsequent loss of prolonged fragrance release in actual usage. Use of commercially available materials eliminates excessive high material cost based on restricted specialty items. Production is simple requiring only a mixing step as compared to complicated processes requiring a special expensive and difficult encapsulation step.

While this invention is not limited to any theory of action, when the fragrance composition is applied to the skin, the fragrance compound oil employed is believed to become entrapped in the film-forming material during evaporation of the volatile solvent. The release of the entrapped fragrance compound is thereby hindered resulting in a reduced release rate. The exact mechanism through which this release works is not fully known; however, it can be understood that several mechanisms may be hypothesized:

a. Reduction of the partial vapor pressure of the fragrance through solubility or chemical binding with the film.
b. Mechanical repression of vapor pressure of the fragrance through an in-situ encapsulation by the film.
c. Release of fragrance bound to film by absorption and subsequent unbinding by cutaneous moisture.

Any fragrance oil that is soluble in the water-ethanol solvent and which is compatible with the film-former so as to give a mutual compatible system may be used. Examples of components found in fragrance oils of the aforementioned type are: musk ketone, ionone, cedarwood terpeneless, aldehyde C-12 lauric, auranthiol, methyl anthranilate, vanillin, bergamot terpeneless, oil of cananga, citral, oil of patchouly, resin Balsam Tolu, musk ambrette, sandalwood oil, geraniol, terpenyl acetate, rhodinol, hydroxycitronellal, oil of orange, oil of geranium, methyl ionone, oil of lavender, phenyl ethyl acetate, rosewood oil, aldehyde C-12 MNA.

Any film-former that is soluble in the water-ethanol solvent and which is compatible with fragrance oil may be used. Film-former materials useful in the production of the fragrance compositions of this invention are ionic and non-ionic derivatives of water-soluble polymers. Examples of suitable film-forming materials are water soluble polymers containing a cationic moiety such as polyvinyl pyrrolidone derivatives such as quaternized polyvinyl pyrrolidone having molecular weight of 50,000 to 1,000,000. Other examples of ionic polymeric film forming materials are cationic cellulose derivatives sold under the trade names of polymer JR (Union Carbide), Klucel GM (Hercules) and ethoxylated polyethyleneimine sold under the trade name PEI 600 (Dow). Examples of suitable non-ionic film forming materials are water soluble cellulosic derivatives such as hydroxymethyl cellulose, hydroxypropyl methylcellulose and hydroxyethyl cellulose.

The fragrance oil, film-former and water-ethanol solvent are of such nature and in such amounts that the fragrance oil is co-dissolved in the water-ethanol solvent along with the film-former. Also, the aforementioned components are in such amounts that when the fragrance composition is applied to the skin, the initial odor strength is adequate and the fragrance oil subsequent to application is released at an appropriate rate so that the desired odor level is maintained for a long period of time.

In general, the fragrance oil is in an amount of 0.01 to 50.0% by weight, and preferably 1.0 to 5.0% by weight of the total weight of the fragrance oil, film-former and water-ethanol solvent components. The film-former is generally in an amount of 0.01 to 20.0% by weight, and preferably 0.1 to 2.0% by weight of the total weight of the fragrance oil, film-former and water-ethanol solvent components. The water-ethanol solvent component is generally in an amount of 30.0 to 99.98% by weight, and preferably 93.0 to 98.99% by weight of the total weight of the fragrance oil, filmformer and water-ethanol solvent components. In the water-ethanol solvent components. In the water-ethanol solvent component, the water is generally in an amount of 1.0 to 59.8% by weight, and preferably 20.0 to 40.0% by weight of the water-ethanol solvent mixture.

In addition to the above-mentioned essential components, i.e., the fragrance oil, film-former and water-ethanol solvent, conventional fragrance composition additives may be incorporated in the compositions of this invention.

Adjuvants, such as glycerine, propylene glycol, etc., may be added to improve humectancy and spreading of the film. Other adjuvants may be added as film plasticizers if needed.

Homologous polymers of different molecular weight (viscosity) may be used to achieve the same effect. As the molecular weight in a homologous polymeric series is increased, the concentration by weight required is decreased. Mixtures of non-homologous polymers each below their respective critical concentration may be used.

In addition to the above variations, adjuvants may be added to obtain special and joint results such as the addition of anti-microbial agents, skin coloring or toning agents, sunscreening agents, and others.

In the manufacture of the fragrance compositions of this invention, the following method is preferably followed. The film-former is added to water and stirred to form a uniform dispersion or solution. To this dispersion or solution is added an appropriate amount of ethanol and the resulting mixture is stirred until a clear solution results. To this solution is added the fragrance oil and the resulting mixture is stirred until a clear solution results.

If the film-former is not easily soluble in ethanol, the above described method should be used in order to ensure a uniform product. If the film-former is easily soluble in ethanol, as an alternative to the method described above, the film-former may be first added to the ethanol and stirred to give a solution thereof, after which the remaining components, i.e., water and fragrance oil are added to the ethanol solution. The water may be added first to the ethanol solution and then the fragrance oil, or the fragrance oil may be added first and then the water.

In order to illustrate the invention by specific example, the following Examples I to VI are given. In the fragrance composition formulations disclosed in the examples which follow, the fragrance compositions were prepared by the hereinbefore-described preferred method wherein first the filmformer is added to water, afterwhich the ethanol and the fragrance oil are added.

EXAMPLE I

| | |
|---|---|
| Quaternized vinyl pyrrolidone copolymer (mol. wt. c100,000) | 4.0 |
| Ethyl Alcohol 190 Proof | 78.2 |
| Fragrance Oil NP13 | 5.3 |
| Water | 12.5 |

Two drops of the test solution (coded) and an equivalent amount of a control solution (coded) prepared without the film-former polymer, were placed on randomized marked areas on the top of each forearm. Each panelist was then allowed to go about unrestricted. After 7½ hours, a group of judges compared the marked areas for residual odor strength. The marked area having the stronger residual odor was given a value of one (1). So that each forearm scored a point, each panelist scored two points. The number of points for the test solution and for the control solution were summed up and compared for significance.

Results for Example I were obtained by adding the scores obtained by five (5) judges on nine panelists were:

| | |
|---|---|
| Example I | 73 |
| Control | 35 |
| | 108 |

Since 73 out of 108 is statistically significant, Example I is concluded to be significantly longer lasting at 7½ hrs.

EXAMPLE II

| | |
|---|---|
| Quaternized vinyl pyrrolidone copolymer (mol. wt. c1,000,000) | 3.0 |
| Ethyl Alcohol 190 Proof | 79.7 |
| Fragrance Oil NP13 | 5.3 |
| Water | 12.0 |

The composition from Example II was compared to a control solution by the same method as used in Example I. Six judges evaluated ten panelists and found 82 preferences out of 120 for a significant prolongation.

EXAMPLE III

| | |
|---|---|
| Ethoxylated Polyethyleneimine | 1.0 |
| Ethyl Alcohol 190 Proof | 79.7 |
| Fragrance Oil NP13 | 5.3 |
| Water | 12.0 |

When applied as in Example I, seven judges evaluated ten panelists finding 84 preferences out of 140 for a significant prolongation.

EXAMPLE IV

| | |
|---|---|
| Quaternized vinyl pyrrolidone copolymer (mol.wt. c1,000,000) | 1.0 |
| Ethyl Alcohol 190 Proof | 79.7 |
| Fragrance Oil NP13 | 5.3 |
| Water | 14.0 |

When applied as in Example I, seven judges evaluated ten panelists finding 88 preferences out of 140 for a significant prolongation.

EXAMPLE V

| | |
|---|---|
| Cationic Cellulosic Polymer | 1.0 |
| Ethyl Alcohol 190 Proof | 74.7 |
| Fragrance Oil NP13 | 5.3 |
| Water | 19.0 |

When applied as in Example I, six judges evaluated eleven panelists finding 86 preferences out of 130 for a significant prolongation.

EXAMPLE VI

| | |
|---|---|
| Hydroxypropyl Methylcellulose (400 centipoise viscosity at 2%) | 1.0 |
| Ethyl Alcohol 190 Proof | 80.0 |
| Fragrance Oil NP13 | 5.3 |
| Water | 13.7 |

When applied as in Example I, seven judges evaluated 12 panelists finding 128 preferences out of 162 for a significant prolongation. (Two responses were out, four responses showed no difference.)

We claim:

1. A fragrance composition having an adequate odor strength when initially applied to the human skin and which odor strength is continued for a long period of time after application comprising a fragrance oil and a film former mutually soluble in a water-ethanol solvent system, the film-former being in an amount of 0.01 to 20.0% by weight of the total weight of the film-former, fragrance oil and water-ethanol solvent components, the fragrance oil being in an amount of 0.01 to 50.0% by weight of the total weight of the film-former, fragrance oil and waterethanol solvent components, the water-ethanol solvent being in an amount of 30.0 to 99.98% by weight of the total weight of the fragrance oil, film-former and water-ethanol solvent components, the water being in an amount of 1.0 to 59.8% by weight of the water-ethanol solvent.

2. A fragrance composition according to claim 1 wherein the film-former is a quaternized vinyl pyrrolidone copolymer.

3. A fragrance composition according to claim 1 wherein the film-former is an ethoxylated polyethyleneimine.

4. A fragrance composition according to claim 1 wherein the film-former is a cationic cellulosic polymer.

5. A fragrance composition according to claim 1 wherein the film-former is hydroxy propyl methyl cellulose.

6. A fragrance composition having an adequate odor strength when initially applied to the human skin and which odor strength is continued for a long period of time after application comprising a fragrance oil and a film-former mutually soluble in a water-ethanol solvent system, the film-former being in an amount of 0.1 to 2.0% by weight of the total weight of the film-former, fragrance oil and water-ethanol solvent components, the fragrance oil being in an amount of 1.0 to 5.0% by weight of the total weight of the film-former, fragrance oil and water-ethanol solvent components, the water-ethanol solvent being in an amount of 93.0 to 98.99% by weight of the total weight of the fragrance oil, film-former and water-ethanol solvent components, the water being in an amount of 20.0 to 40.0% by weight of the water-ethanol solvent.

7. A fragrance composition according to claim 6 wherein the film-former is a quaternized vinyl pyrrolidone copolymer.

8. A fragrance composition according to claim 6 wherein the film-former is an ethoxylated polyethyleneimine.

9. A fragrance composition according to claim 6 wherein the film-former is a cationic cellulosic polymer.

10. A fragrance composition according to claim 6 wherein the film-former is hydroxy propyl methyl cellulose.

\* \* \* \* \*